US012796918B2

(12) United States Patent
Kumagai et al.

(10) Patent No.: US 12,796,918 B2
(45) Date of Patent: Nov. 17, 2026

(54) NON-TRANSITORY COMPUTER-READABLE STORAGE MEDIUM AND OPHTHALMIC IMAGE PROCESSING APPARATUS

(71) Applicant: NIDEK CO., LTD., Gamagori (JP)

(72) Inventors: Yoshiki Kumagai, Gamagori (JP); Ryosuke Shiba, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 1177 days.

(21) Appl. No.: 17/852,490

(22) Filed: Jun. 29, 2022

(65) Prior Publication Data

US 2023/0000348 A1 Jan. 5, 2023

(30) Foreign Application Priority Data

Jul. 5, 2021 (JP) ................................ 2021-111847

(51) Int. Cl.

| | |
|---|---|
| ***A61B 3/12*** | (2006.01) |
| ***A61B 3/00*** | (2006.01) |
| ***A61B 3/14*** | (2006.01) |
| ***G06T 5/40*** | (2006.01) |
| ***G06T 7/90*** | (2017.01) |

(52) U.S. Cl.

CPC .............. *A61B 3/12* (2013.01); *A61B 3/0058* (2013.01); *A61B 3/14* (2013.01); *G06T 5/40* (2013.01); *G06T 7/90* (2017.01); *G06T 2207/10024* (2013.01); *G06T 2207/30041* (2013.01)

(58) Field of Classification Search

CPC ........... A61B 3/0058; A61B 3/12; A61B 3/14; G06T 5/40; G06T 7/90; G06T 2207/10024; G06T 2207/30041; H04N 1/60; H04N 1/6058

See application file for complete search history.

(56) References Cited

U.S. PATENT DOCUMENTS

| | | | |
|---|---|---|---|
| 2006/0012839 | A1 | 1/2006 | Fukuda |
| 2013/0028484 | A1 | 1/2013 | Wada et al. |
| 2020/0100672 | A1 | 4/2020 | Murase et al. |

FOREIGN PATENT DOCUMENTS

| | | | |
|---|---|---|---|
| JP | 2006-33383 | A | 2/2006 |
| JP | 2013-48889 | A | 3/2013 |
| JP | 2019-208708 | A | 12/2019 |
| JP | 2020-54479 | A | 4/2020 |

OTHER PUBLICATIONS

Office Action issued on Feb. 12, 2025 by the Japanese Patent Office in corresponding JP Patent Application No. 2021-111847.

Office Action issued Oct. 22, 2024 by the Japan Patent Office in Japanese Patent Application No. 2021-111847.

*Primary Examiner* — Jack Dinh

(74) *Attorney, Agent, or Firm* — Sughrue Mion, PLLC

(57) ABSTRACT

An ophthalmic image processing apparatus includes a processor. The processor acquires a first image as a color fundus image, and corrects a pixel value of at least any color component in the first image, based on color gamut information for specifying a predetermined color gamut to be applied to a color fundus image, to generate a color gamut-corrected image.

11 Claims, 9 Drawing Sheets

NON-TRANSITORY COMPUTER-READABLE STORAGE MEDIUM AND OPHTHALMIC IMAGE PROCESSING APPARATUS

CROSS-REFERENCE TO RELATED APPLICATIONS

This application claims priority from Japanese Patent Application No. 2021-111847 filed on Jul. 5, 2021, the entire subject-matter of which is incorporated herein by reference.

TECHNICAL FIELD

The present disclosure relates to a non-transitory computer-readable storage medium storing an ophthalmic image processing program for processing a fundus image of a subject eye, and an ophthalmic image processing apparatus.

BACKGROUND ART

For a long time, in the field of ophthalmology, color fundus images (hereinafter, referred to as fundus photographs) captured by fundus cameras have been used in fundus examination.

In recent years, devices with a high confocal feature compared with conventional fundus cameras have become widespread in ophthalmic facilities. Color fundus images captured by the devices are also utilized in fundus examination. In a color fundus image captured by a device having a high confocal function, for example, each part is depicted with a higher contrast, but a color tint is different from that of a fundus photograph.

As a technique for bringing a color tint of a color fundus image captured by a device having a high confocal system closer to that of a fundus photograph, JP-A-2020-054479 discloses a technique in which a color tone of a color fundus image captured by a device having a high confocal system is corrected on the basis of a predetermined histogram target pattern for each color. According to this, in the device of the high confocal type, a color fundus image having a constant color tone is generated regardless of a wavelength of illumination light, an individual difference in a fundus shape, and an alignment state.

However, due to a difference between an imaging method of a fundus camera and an imaging method different from that, even if a color tone of a fundus image acquired by a device employing the latter method is corrected by using the method in JP-A-2020-054479 described above, unnatural color development may occur in a part of the image when a fundus photograph is used as a reference. The color development can be a useful index for understanding a condition of a fundus, but may give a sense of discomfort to an examiner who is accustomed to fundus photographs.

SUMMARY OF INVENTION

An object of the present disclosure is to provide a non-transitory computer-readable storage medium recording an ophthalmic image processing program capable of generating a color fundus image with less sense of discomfort to an examiner, and an ophthalmic image processing apparatus.

A first aspect of the present disclosure is a non-transitory computer-readable storage medium storing an ophthalmic image processing program having instructions which, when the ophthalmic image processing program is executed by a processor of a computer, cause the computer to perform:

- a first image acquisition step of acquiring a first image as a color fundus image; and
- a color gamut-corrected image generation step of correcting a pixel value of at least any color component in the first image, based on color gamut information for specifying a predetermined color gamut to be applied to a color fundus image, to generate a color gamut-corrected image.

A second aspect of the present disclosure is an ophthalmic image processing apparatus including a processor configured to:

- acquire a first image as a color fundus image; and
- correct a pixel value of at least any color component in the first image, based on color gamut information for specifying a predetermined color gamut to be applied to a color fundus image, to generate a color gamut-corrected image.

DESCRIPTION OF EMBODIMENTS

[Outline]

Figure 1:
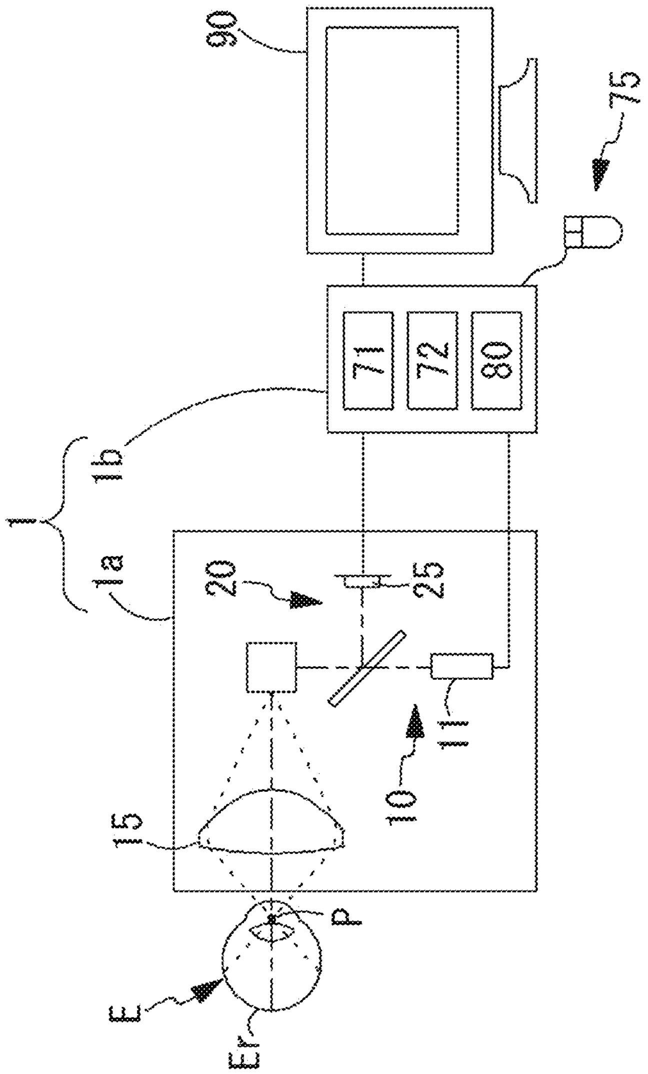
FIG. 1 is a diagram showing a schematic configuration of a fundus imaging device according to an embodiment.

Hereinafter, the present disclosure will be described on the basis of an embodiment. For convenience, in the following description, unless otherwise specified, the processing content of an ophthalmic image processing program according to the embodiment and an ophthalmic image processing method will be described as being executed by a computer. The computer may be an ophthalmic image processing apparatus including an ophthalmic imaging device, or may be an ophthalmic image processing apparatus separate from the ophthalmic imaging device.

The ophthalmic image processing program of the present embodiment causes a computer to execute at least a first image acquisition step and a color gamut-corrected image generation step. In the first image acquisition step, a color fundus image is acquired as a first image. In the color gamut-corrected image generation step, a pixel value of at least any color component in the first image is corrected on the basis of color gamut information. As a result, a color gamut-corrected image is generated from the first image. The color gamut information is information for specifying a predetermined color gamut to be applied to a color fundus image. Therefore, in the color gamut-corrected image, a color tint of each tissue is expressed in a predetermined color gamut.

A color gamut specified in the color gamut information in the present embodiment is different from a color reproduction gamut (color gamut) of each image output device. That is, the color gamut specified in the color gamut information is not derived from an image output device such as a display and a printer. Therefore, a color gamut-corrected image is expressed in a predetermined color gamut that is different from the original color gamut of the first image and the color gamut derived from an image output device such as a display and a printer.

In the present embodiment, the color gamut information may be information for specifying a target hue section after correction (after color gamut conversion). More specifically, the color gamut information may be information for defining a target color gamut after correction (after color gamut conversion), information indicating a correspondence between color gamuts before and after correction, such as a mapping table, or other information. In the present embodiment, a pixel value of at least any color component in the first image is corrected such that a color exceeding from the target hue section in the first image is included in the target hue section, or a difference from the target hue section is reduced. As a result, in a color gamut-corrected image, unnatural colors can be appropriately reduced with respect to a target.

The first image may be a color fundus image according to a first imaging method. The target hue section in the color gamut information may be appropriately determined. For example, a hue section of a color fundus image according to a second imaging method different from the first imaging method may be defined as a target color gamut. In this case, the target color gamut is defined in order to suppress a difference in hue between a color fundus image captured according to the second imaging method and the first image, and complete matching with a color gamut in the color fundus image captured according to the second imaging method is not necessarily required. A color gamut corresponding to the second imaging method may be determined on the basis of an average and a variance of hues of respective pixels in the color fundus image captured according to the second imaging method.

The first imaging method may be a confocal method, and the second imaging method may be a non-confocal method. There are some differences between the confocal method and the non-confocal method as follows. For example, in the confocal method, unnecessary scattered light is suppressed from being guided to a light receiving element compared with the non-confocal method such as that of a fundus camera. Therefore, the first image is an image having excellent contrast. For example, in the confocal method, a light source having a narrow wavelength range (for example, a monochromatic light source) is used compared with a white light source such as a flash lamp widely used in a fundus camera. Since the fundus has different spectral reflection characteristics for each tissue (for example, for each layer), emphasized tissues may be different between color fundus images acquired according to the two imaging methods.

In a case where an imaging optical system employs the confocal method, a color tone (balance of each color component) of the entire image of a fundus image may be different for each imaging operation depending on differences in imaging conditions such as alignment and focus. Therefore, even in a case where a specific subject eye is imaged, it is difficult to stabilize a color tone of the entire image in each imaging operation.

On the other hand, in the present embodiment, regarding the first image, the first image may be acquired by converting a color fundus image (referred to as an original image) captured according to the confocal method through a process different from that in the color gamut-corrected image generation step. For example, the conversion may be performed manually or automatically.

As a specific example, a pixel value of each color component in the original image may be corrected on the basis of a predetermined histogram target pattern for each color component. Consequently, regardless of a difference in imaging conditions, the first image becomes an image having a color tone defined by a predefined histogram target pattern for each color component. The target pattern may be, for example, a target pattern for coming closer to a color tint of a fundus photograph.

However, even if the color tone of the first image is corrected in advance, a color tint of a part of the image may be different from a target color tint.

For example, even if the color tone of the first image is corrected in advance to come closer to the color tint of the fundus photograph, the color development in a tissue having a different shape from the surroundings such as an optic nerve head or a lesion is different from that in the fundus photograph and thus tends to be unnatural. More specifically, a part of the tissue or the lesion may have a relatively small red component to be depicted green. It is considered that this phenomenon is caused by a difference between the confocal method and the non-confocal method, which is exemplified above or another factor.

On the other hand, the first image acquired according to the confocal method is corrected on the basis of a color gamut corresponding to the color fundus image acquired according to the non-confocal method, and as a result, the occurrence of a location having an unnatural color tint is reduced compared with the color fundus image acquired according to the non-confocal method.

In this case, it is preferable that a pixel value of at least the red component in the first image is corrected on the basis of the color gamut information. That is, since the red component is relatively small in a portion of the first image that is depicted green, the pixel value of the red component is corrected to a high luminance side, so that a tissue is depicted in a more natural color when the color fundus image according to the non-confocal method is used as a reference.

In the present embodiment, a GUI for accepting a change operation for a color gamut specified by the color gamut information may be displayed. The color gamut information may be changeable on the basis of a change operation via the GUI. Consequently, an examiner can adjust the color gamut-corrected image to a desired color tint.

In the present embodiment, the color gamut-corrected image and a color component image corresponding to the first image are output to an image output device such that the color component image which is a fundus image for each color component in the first image is displayed together with the color gamut-corrected image. Here, in the fundus image for each color component in the color gamut-corrected image, an image that does not originally exist may be drawn in a pixel of which a color component has been corrected as a result of color gamut correction. Therefore, upon displaying the color component image together with the color gamut-corrected image, an examiner can appropriately check the color component image by using a color component image of the first image can be used as the color component image.

In the above embodiment, the color gamut information has been described as information indicating a color gamut corresponding to the second imaging method, but is not necessarily limited to this. For example, the color gamut information may be set on the basis of the first image. For example, if it is empirically clear that a natural color (that is, a color included in a desired hue section) is dominant in the first image, it is considered that a hue section is obtained on the basis of an average, a variance, or the like of hue of each pixel in the first image such that an unnatural color, which is a deviation value from the hue section, can be excluded. Therefore, it is considered that a color gamut-corrected image in which unnatural colors in the first image are reduced can be generated even if a color gamut is corrected by using the color gamut information based on the first image as described above.

Example

<Overall Configuration>

A fundus imaging device 1 (hereinafter, abbreviated to "the present device 1") according to an embodiment includes at least imaging optical systems 10 and 20 and an image processor 80. The present device 1 includes the image processor 80 to function as a computer that executes various types of image processing. The image processor 80 may also be shared by a processor that controls an operation of the entire device. The image processor 80 may be separate from a processor that controls an operation of the entire device. An ophthalmic image processing program may be stored in a memory accessible from a processor of the image processor 80.

As shown in FIG. 1, the present device 1 is roughly divided into an optical unit 1*a* and a control unit 1*b*. The imaging optical systems 10 and 20 may be stored in the optical unit 1*a*, and the image processor 80 may be stored in the control unit 1*b*. The control unit 1*b* has various memories 72 in addition to a processor (CPU) 71. The ophthalmic image processing program may be stored in the memory 72. An operation unit 75 (user interface) may be connected to the control unit 1*b*. The operation unit 75 may be a pointing device such as a mouse and a touch panel, or may be another user interface. For example, a PC may be used as the control unit 1*b*.

The present device 1 may have a monitor 90. For example, a captured fundus image is displayed on the monitor 90. In addition, various GUIs may be displayed on the monitor 90.

<Imaging Optical System>

The imaging optical systems 10 and 20 capture at least a color fundus image, which is a kind of fundus image. In the present embodiment, the fundus image is a front image of the fundus. In the color fundus image, each pixel has color information. The imaging optical systems 10 and 20 include an irradiation optical system 10 and a light receiving optical system 20 (refer to FIG. 1). The imaging optical systems 10 and 20 may capture a monochrome fundus image.

The irradiation optical system 10 irradiates the fundus with a plurality of pieces of monochromatic light having different wavelengths. The light receiving optical system 20 has at least a light receiving element 25 that receives a plurality of pieces of monochromatic light reflected from the fundus. A signal from the light receiving element 25 is input to the image processor 80, and as a result, a color fundus image is generated by the image processor 80. In the light receiving optical system 20, a plurality of light receiving elements 25 may be provided for each wavelength of monochromatic light. In this case, a plurality of pieces of monochromatic light reflected from the fundus having different wavelengths may be received simultaneously by the plurality of light receiving elements 25 by the plurality of pieces of light reflected from the fundus. A plurality of pieces of light reflected from the fundus having different wavelengths may be received by one light receiving element 25 in a time division manner (in other words, at different timings). As the light receiving element 25, a point light receiving element, a one-dimensional imaging element (line sensor), a two-dimensional imaging element, or the like may be used. A sensor to be used is selected as appropriate according to an imaging method.

The irradiation optical system 10 may have a light source 11 for each wavelength. For example, as the light source 11, any one of various light sources such as a monochromatic LED and a laser light source may be used. Here, "monochromatic light" has a narrow meaning of light that cannot be decomposed into spectra, but is not necessarily limited to this in the present disclosure. The "monochromatic light" in the present disclosure may have a width of wavelength distribution to the extent that the light is handled as a specific color in the technical field of the fundus imaging device. However, the width of the wavelength distribution in monochromatic light is narrow enough to be clearly distinguishable from white light in the technical field of fundus imaging device.

For example, the imaging optical systems 10 and 20 may irradiate the fundus with three colors of red (R), green (G), and blue (B) when a color fundus image is captured. In this case, infrared (IR) light may be applied to the fundus in addition to or instead of R light. Here, when a color fundus image is captured, light of three or four colors of light is applied to the fundus, but the present disclosure is not limited to this, and the light applied to the fundus may be light of two colors or light of five or more colors. The above color combination is only an example, and a color fundus image may be captured by using another color combination.

The imaging optical systems 10 and 20 may be confocal optical systems. In a case of the confocal optical system, the irradiation optical system 10 has an optical scanner, collects illumination light (here, monochromatic light) in a point-like or line-like manner on the fundus, and scans the fundus with the illumination light by using the optical scanner. The light receiving optical system 20 is provided with a harmful light removing portion (for example, a pinhole and a slit aperture) at a fundus conjugate position. The harmful light removing portion guides fundus reflected light from a region irradiated with the illumination light to the light receiving element 25, and removes the rest. As a result of sequential light reception by the light receiving element 25, a front image of the fundus is acquired. In a line scan method, the light receiving element 25 may also serve as a harmful light removing portion. In this case, a line sensor used as the light receiving element 25 is disposed at the fundus conjugate position. An example of a non-confocal imaging optical system is an optical system of a general fundus camera. For more details of the confocal optical system, refer to, for example, JP-A-2016-059539 filed by the present applicant. This document discloses a scanning laser ophthalmoscope, which is an example of a fundus imaging device having a confocal optical system.

<Image Processor>

As described above, the image processor 80 generates a fundus image on the basis of the signal from the light receiving element 25. In the present embodiment, at least a color fundus image is generated as the fundus image. However, the present disclosure is not limited to this, and the image processor 80 may additionally generate a monochrome fundus image on the basis of the signal from the light receiving element 25.

The image processor performs a correction process for bringing the color fundus image captured by the present device 1 employing the confocal method closer to a color tint of a fundus photograph (a color fundus image captured according to the non-confocal method by using white light). For example, the image processor generates a first image (color tone-corrected image) and a second image (color gamut-corrected image) in a case where a color fundus image is captured. The first image and the second image are generated by correcting a pixel value of an original image by using the color fundus image obtained as a result of imaging as a processing target (that is, the original image). The first image and the second image in the present example are both color fundus images having color components of R, G, and B.

In the following description, for convenience of the description, a color that does not exist empirically in a fundus photograph will be referred to as an "unnatural color", and an existing color will be referred to as a "natural color". However, the distinction between natural and unnatural is only a convenience to show a color tint difference between different imaging methods, and it should be noted that in each imaging method, the distinction is not related to the question of whether or not original characteristics are properly depicted.

A method of color correction for a color fundus image of the present example will be described with reference to FIGS. 2 to 8C.

Figure 2:
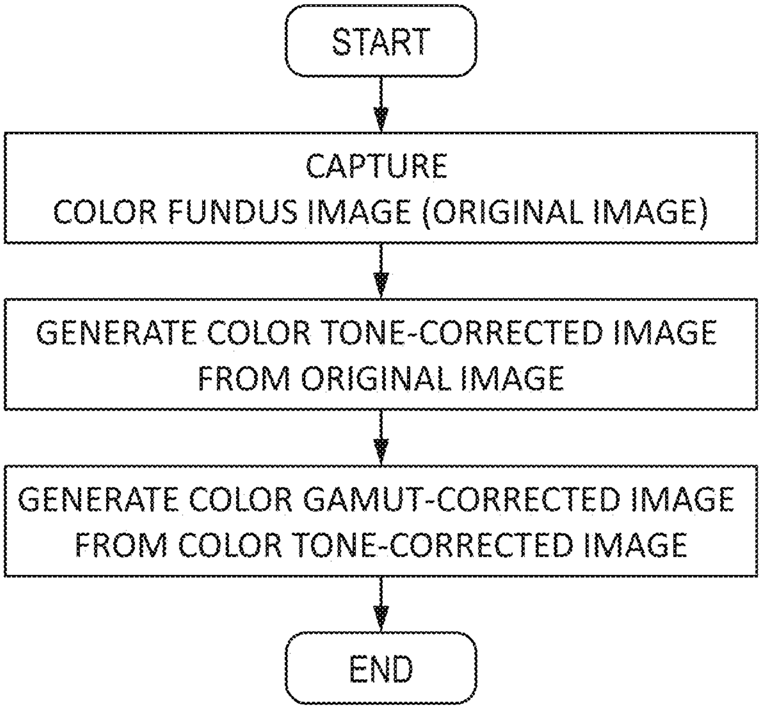
FIG. 2 is a flowchart showing an ophthalmic image processing method according to the present embodiment.

In the present example, as shown in FIG. 2, first, a color fundus image as an original image is captured, and then a color tone of the original image is corrected to generate and acquire a first image. By correcting a color gamut in the first image, a second image is generated and acquired.

Figure 3:
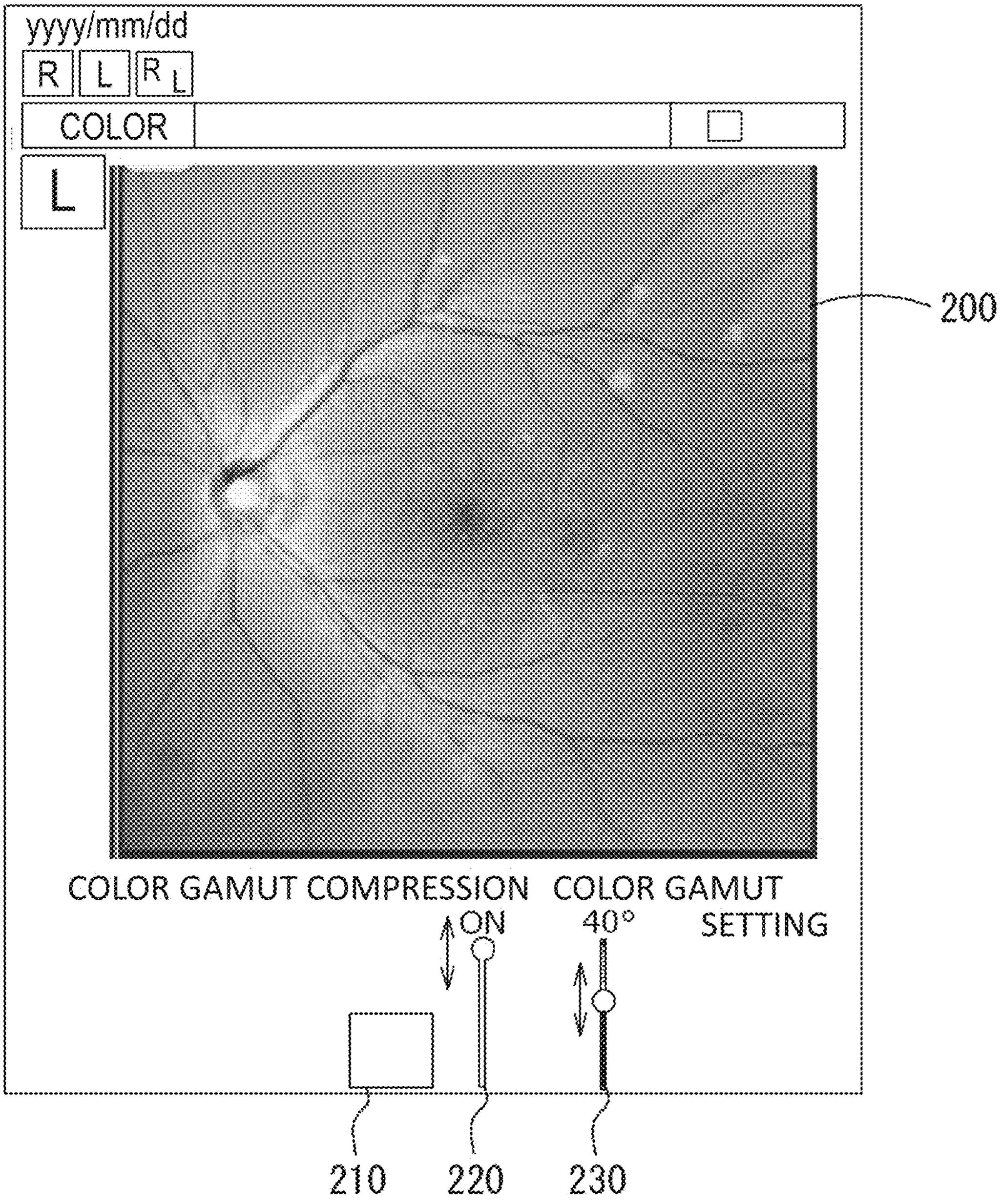
FIG. 3 is a diagram showing a GUI for color correction and a fundus image display layout.

In this case, as shown in FIG. 3, a color fundus image 200, the GUI 210 for color tone correction, and GUIs 220 and 230 for color gamut correction are displayed on a screen. A color in the color fundus image 200 displayed on the screen is corrected according to an operation on the GUIs 210 to 230.

First, the original image is displayed on the screen as the color fundus image 200. An examiner first operates the GUI 210 for color tone correction. Consequently, a color tone of the original image is corrected, and thus the first image is generated and displayed on the screen.

<Color Tone Correction>

Since the color fundus image acquired by the imaging optical systems 10 and 20 in the present example uses monochromatic light as illumination light, compared with an image captured by using white light, such as a fundus photograph, reflection characteristics of the fundus easily affect a color tone, and the color tone is difficult to stabilize. Since the imaging optical systems 10 and 20 in the present example have higher confocal characteristics than those of a fundus camera, an individual difference in the fundus shape and the alignment state greatly affect the color tone. As a result, the color fundus image acquired by the imaging optical systems 10 and 20 in the present example is difficult to reproduce with a constant color tone. In the field of fundus examination, as a result of many years of utilization of color fundus images captured with white light, color tones of color fundus images captured with white light have widely penetrated examiners. In comparison with this, it cannot be said that color tones of color fundus images captured by using monochromatic light have sufficiently penetrated examiners.

In contrast, in the present embodiment, the first image (color tone-corrected image) is a color fundus image expressed in a predetermined color tone regardless of a subject eye and imaging conditions. The first image is generated by correcting a grayscale value of each pixel in an original image such that a feature value based on a distribution of grayscale values of pixels in the original image, which is the feature value for each color component, is fitted to a feature value predetermined as a target pattern for each color component.

The target pattern in the present example represents a histogram pattern of each color component (each color component of R, G, and B) in a fundus photograph. A light source that emits white light may be any of a xenon lamp, a white LED, or the like. The color fundus image may be, for example, an image captured by a fundus camera. For example, the target pattern may be predetermined on the basis of an average luminance distribution in an actual fundus photograph.

A feature value defined as a target pattern is a value that defines a histogram based on a distribution of grayscale values of each pixel. As an example, in the present example, a target value of brightness and a target value of contrast may be predetermined for each color component as feature values. As an example, as the target value of brightness, any one of an average value, a median value, and a mode value of grayscale values in a target grayscale distribution may be used. As the target value of contrast, any value of standard deviation, variance, and full width at half maximum in a target grayscale distribution may be used.

Figure 4:
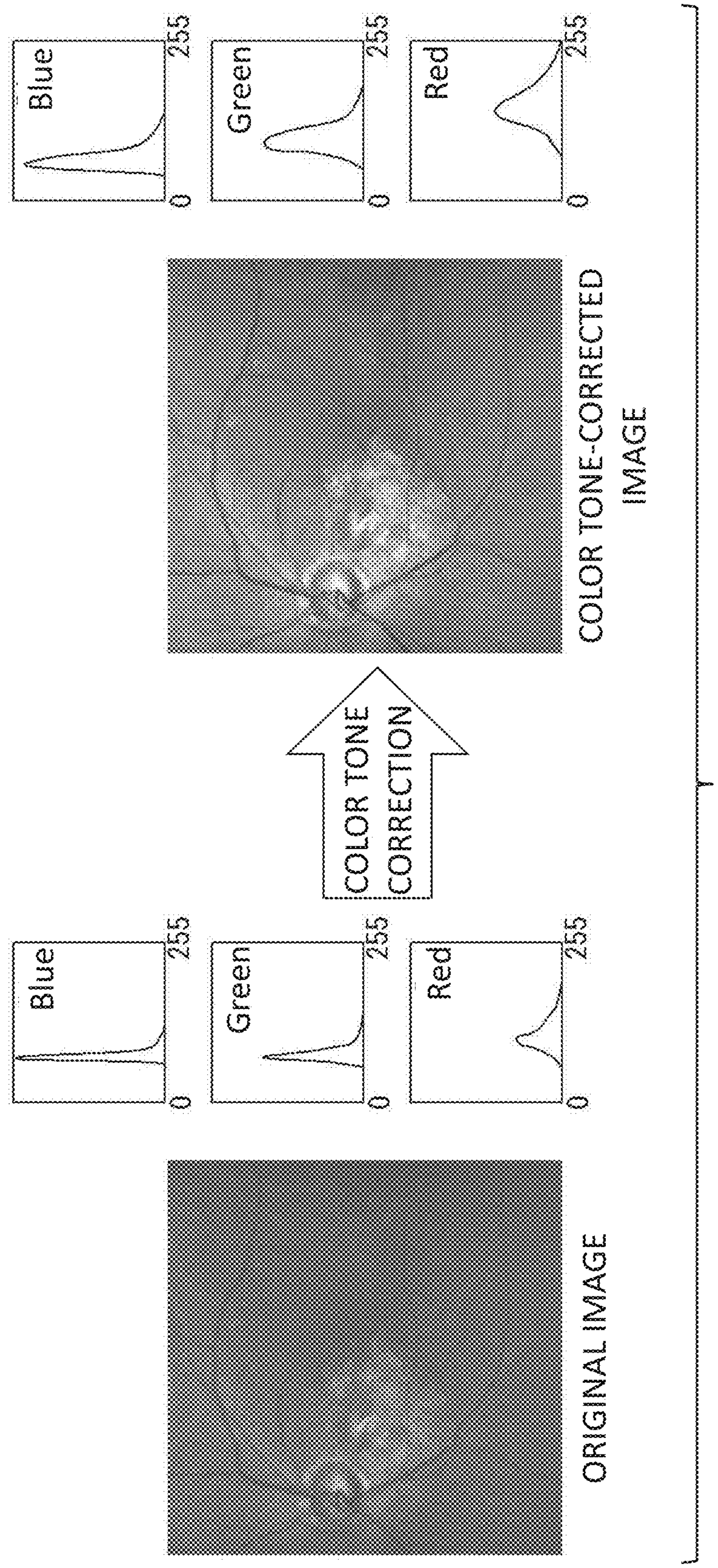
FIG. 4 is a diagram for describing a color tone correction method, and shows fundus images before and after correction in a case where a target pattern is used, and a histogram of each channel.

With reference to FIG. 4, features of a color tone-corrected image, in which a color tone is corrected by applying a target pattern in the present example, will be described in detail. Each graph in FIG. 4 shows a histogram for each color component (for each color component of R, G, and B).

In the color tone-corrected image shown in FIG. 4, the histogram for each color component is corrected so as to fit a target pattern defined by the following target values.

Each target value is in units of grayscale values in 256 grayscales.

[Target Value of Brightness (Average Value of Grayscale Distribution)]

R: 122
G: 66
B: 32

[Target Value (Standard Deviation) of Contrast]

R: 40
G: 27.5
B: 16.6

These target values, shown as an example, are set on the basis of a fundus photograph. The first image acquired as described above is meaningful because the reproducibility is guaranteed with a color tone familiar to the examiner.

<Color Gamut Correction>

However, the first image is depicted in a color that does not give a sense of uncomfortable when compared with a fundus photograph or the like, but may be depicted in an unnatural color that is unfamiliar in the fundus photograph in a partial region of a part of the image. As an example, an unnatural color is likely to occur in a tissue having a shape different from the surroundings such as the optic nerve head, a lesion, or the like. In a portion where unnaturalness occurs, there is a tendency for the red component to be less than in the fundus photograph, and as a result, the optic nerve head or the like is depicted greenish (or bluish) that is unfamiliar in the fundus photograph, and thus a sense of discomfort is caused.

However, in the first image, a greenish tinge of the optic nerve head or the lesion can be used as an index regarding a shape of the optic nerve head or the presence or absence of the lesion. Therefore, it may be possible to select whether to display the first image or the second image according to an operation of the examiner. Therefore, in the present example, the color gamut correction can be enabled/disabled via the GUI 220.

In a case where the GUI 220 is operated and the color gamut correction is enabled, color information of the first image is corrected, and the second image is displayed on the screen as the color fundus image 200.

According to the study of the present inventor, an unnatural color development is reduced by supplementing the red component to an unnatural color region (a region expressed greenish). However, for example, if the balance of the red component in the entire image is changed, most of colors of the image expressed in natural colors in the first image will change.

In contrast, in the present example, the second image is generated by correcting a pixel value of at least any color component in the first image on the basis of a predetermined color gamut. In the present example, correction is performed by clipping the color gamut of the first image (details will be described later) on the basis of the color gamut information indicating a predetermined color gamut. Here, the color gamut information is a predetermined color gamut to be applied to a color fundus image, and in the present example, a color gamut as a target (hereinafter, referred to as a "target color gamut" for convenience) is specified. The target color gamut does not depend on hardware performance (that is, for example, a color reproduction gamut on the monitor 90) of an image output device.

The target color gamut indicated by the color gamut information may be set empirically. For example, the target color gamut in the present example may be set on the basis of a hue (an average value of hue variance) in the first image in which an unnatural color region does not occur. According to this, since the first image is an image of which a color tone is close to that of the fundus photograph, the target color gamut is indirectly set in consideration of the hue section of the color fundus image. The target color gamut may be set on the basis of a hue (an average value of hue variance) in the fundus photograph. Since an unnatural color in the first image does not exist in the target fundus photograph or the like, some examiners feel a sense of discomfort, and such a color is unlikely to be included in the hue section in the fundus photograph or the like. On the other hand, since most of the pixels in the first image are depicted in natural colors, most of these pixels are likely to be included in the hue section in the fundus photograph or the like. Therefore, unnatural colors in the first image can be appropriately excluded from the target color gamut set in consideration of the hue section in the fundus photograph or the like, and most of the colors used in the first image are included in the target color gamut of the present example almost as they are.

Here, with reference to FIG. 5, a color gamut correction method in the present example will be described in detail. In the present example, a color gamut is corrected through clipping. In the clipping shown in the present example, a pixel having the color information outside the target color gamut is corrected to have a color of a color gamut boundary in the target color gamut.

Figure 5:
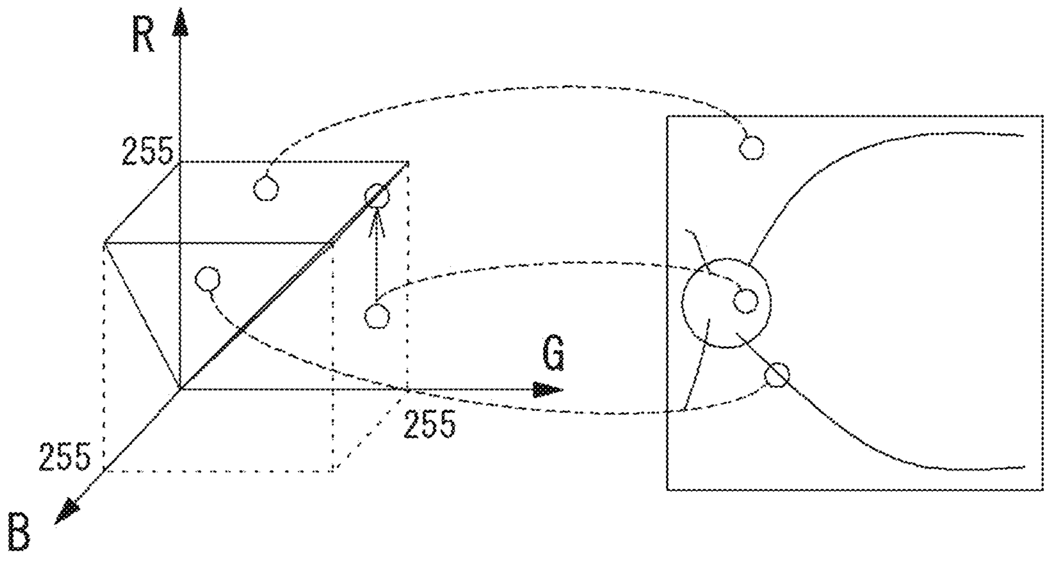
FIG. 5 is a diagram for describing clipping as a color gamut correction method in an Example.

The graph on the left side of FIG. 5 shows an example of color gamut information on a color space. In FIG. 5, a region of the cube surrounded by the dotted line shows the original color gamut in which an image can be expressed.

On the other hand, a region of the quadrangular pyramid surrounded by the solid line indicates the target color gamut. As an example, the region of the quadrangular pyramid in FIG. 5 corresponds to a hue section in which the hue H takes a value from −60° to +60° in the HSV color space. In the hue section, an image is expressed in colors in the range from magenta to yellow. Each pixel in a general fundus photograph is expressed by this hue section. However, the target color gamut is not necessarily limited to this. For example, the target color gamut may be set on the basis of an average and a variance of the hue of each pixel in an actual fundus photograph or the like.

In FIG. 5, the fundus image on the right side of the graph shows a fundus image (that is, the first image in the present example) that is a target of color gamut correction. In the color gamut correction process of the present example, it is determined for each pixel of the first image whether or not color information of the pixel is outside the target color gamut. In this determination, pixel values of R, G, and B of each pixel may be referred to when comparing with the target color gamut, or a value of H may be referred to by converting each pixel into HSV.

A value of the hue H can be obtained from R, G, and B by the conversion formula shown as the following equation (1). That is, the hue H is derived on the basis of the ratio of R, G, and B.

$$H = \begin{cases} 60 \times \dfrac{G-R}{\max(R,G,B)-\min(R,G,B)} + 60, & (\min(R,G,B)=B) \\ 60 \times \dfrac{B-G}{\max(R,G,B)-\min(R,G,B)} + 180, & (\min(R,G,B)=R) \\ 60 \times \dfrac{R-B}{\max(R,G,B)-\min(R,G,B)} + 300, & (\min(R,G,B)=G) \end{cases} \quad (1)$$

Here, the number of unnatural colors in the first image is sufficiently small. In particular, in the present example, the number is sufficiently small in combination with the color tone correction performed in advance. For example, a pixel having such a small number of colors, such as a pixel in the optic nerve head in the fundus image in FIG. 5, is determined to be outside the target color gamut in the first image, and a pixel value of the pixel is changed to be included in the target color gamut. In this case, in the present example, a pixel value of at least the red component is changed to a high luminance side. In the present example, the pixel value is changed on the basis of the following equation (2).

$$R' = \max\{R,G,B\} \quad (2)$$

Here, R' on the left side of equation (2) is a pixel value of a corrected R component. R, G, and B on the right side of equation (2) are pixel values of the respective color components before correction. According to equation (2), a pixel value of only the R component is changed for a pixel determined to have color information outside the target color gamut and is thus corrected to a color of the color gamut boundary.

As in the present example, when the target color gamut is defined as the hue section from −60° to +60° of the hue H in the HSV color space, a grayscale value of the R component is always a value on the low luminance side with respect to at least one of G and B grayscale values outside the target color gamut. Therefore, even if equation (2) is applied to all the pixels of the first image without determining whether or not the pixels are outside the target color gamut in the first image, the same result as when the determination is performed can be obtained. Therefore, the above determination is not always necessary depending on the setting of the target color gamut.

On the other hand, for example, pixels determined to be inside the target color gamut in the first image, such as pixels corresponding to blood vessels or many fundus tissues in the fundus image in FIG. 5, are maintained to have their pixel values. Since such pixels occupy a large number in the first image, the color information of the pixels is maintained in the second image.

As described above, the color tone correction process can be restricted to a pixel having an unnatural color in the first image, and a color in which the pixel is expressed can be replaced with a color in the range from magenta to yellow (that is, a color that does not give a sense of discomfort when the fundus photograph is used as a reference). As a result, the color fundus image captured by the present device 1 is appropriately expressed while using only natural colors.

<Manual Correction>

In the present example, the target color gamut can be further set (changed) on the basis of a user's operation. For example, an operation of setting (changing) the target color gamut is accepted via the GUI 230. In the present example, the GUI 230 is a slider, and the hue section is set by moving a knob along an arrow. In the present example, the hue section of hue H generally has two end points on the blue side and on the green side, but since there is almost no blue in the first image, the blue side has a fixed value (−60° in the present example), and the end point on the green side is changed via the GUI 230. In the GUI 230, an adjustment range of the end point on the green side is defined between 0° and 60°. Generally, a hue section of a certain hue is in a range of −180° to 180°, but the hue section of the fundus photograph is a part thereof as described above. In the present example, since the adjustment range is limited to the necessary and sufficient adjustment range for reproducing a color tint of the fundus photograph, an examiner can appropriately adjust a target hue section.

The second image of which the hue section is changed on the basis of an operation on the GUI 230 is sequentially displayed on the screen. In the present example, a value indicating an end point of the hue section after setting is displayed in conjunction with movement of the knob of the GUI 230. In the GUI 230, a slider is displayed in a color corresponding to the set hue section (with a color gradation). Consequently, it becomes easier for an examiner to intuitively understand the color gamut after setting. As a result, a user can intuitively change the color fundus image to a desired color tint.

Figure 6:
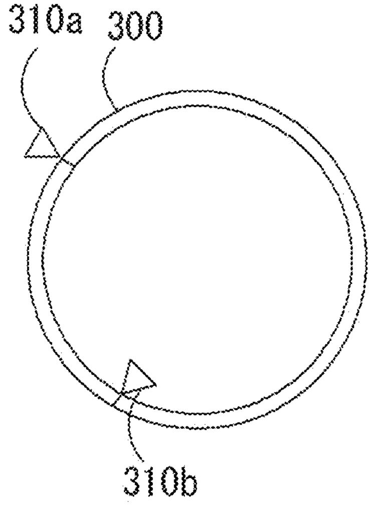
FIG. 6 is a diagram showing a GUI for manually adjusting a target color gamut.

A GUI 300 shown in FIG. 6 may be used instead of the GUI 230. The GUI 300 shown in FIG. 6 imitates a hue wheel, and a user manually moves end points 310*a* and 310*b* between colors. A hue section between the two end points 310*a* and 310*b* is set as the target color gamut. In the present example, the second image with the hue section changed on the basis of the operation is sequentially displayed on the screen. As a result, a user can intuitively change the color fundus image to a desired color tint.

Here, for example, in the description of FIG. 5, in the preset target color gamut is the hue section from −60° to +60° of the hue H, in an actual fundus photograph, the target color gamut tends to be expressed in a narrower hue section. Therefore, in order to depict the color fundus image captured by the present device 1 in a color close to that of the fundus photograph, a target section may be narrowed to the hue section from −60° to +60° of the hue H. In this case, a pixel value is changed on the basis of the following equation (3).

$$R' = \begin{cases} \dfrac{60G + (f(H) - 60)B}{f(H)} & (H < 180,\ f(H) \le 60) \\ \dfrac{-60B + (f(H) - 300)G}{f(H) - 360} & (H \ge 180,\ f(H) \ge 300) \end{cases} \quad (3)$$

Here, f(H) is a target hue (target value of hue) of a color after conversion using equation (3). f(H) is represented by equation (4).

$$f(H) = \begin{cases} H(H \le H_G,\ H \ge H_B) \\ H_G(H_G < H < 180) \\ H_B(180 \le H < H_B) \end{cases} \quad (4)$$

Figure 7:
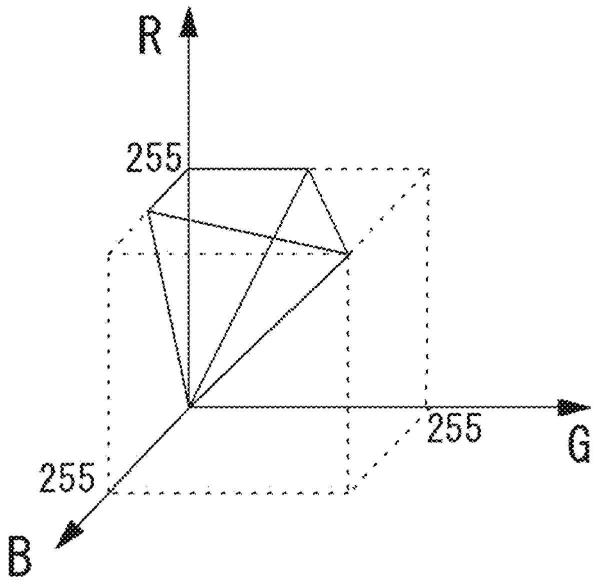
FIG. 7 is a diagram showing an example of an adjusted target color gamut.

Here, H is a hue of a pixel before conversion. $H_B$ is closer to blue between the end points 310*a* and 310*b* of the hue section, while $H_G$ is the rest closer to green. The target color gamut in this case is shown in FIG. 7. Depending on a combination of the setting of the hue section and a pixel value before conversion, a pixel value after conversion may exceed the maximum value that can be expressed (R'>255), but in this case, may be replaced with the maximum value (R'=255).

Consequently, even if the target color gamut is changed, a pixel having color information outside the target color gamut is appropriately corrected to a color of the color boundary in the target color gamut by a changing at least a pixel value of the red component.

<Simultaneous Display of Second Image and Color Component Image of Each Color Component>

In the present example, a color fundus image may be displayed together with a monochrome fundus image (color component image) corresponding to each color component. In this case, the color fundus image and the color component image may be simultaneously displayed to be arranged on the same screen, or may be switched and displayed in one window.

The spectral reflectances of light of red (R), green (G), and blue (B) applied from the present device 1 are different for each tissue (for example, for each layer). Thus, different characteristics can be depicted in respective color component images corresponding to red (R), green (G), and blue (B). Therefore, by displaying the color component image corresponding to each color component together with the color fundus image, an examiner can ascertain a structure of the fundus from various angles.

Figure 8A:
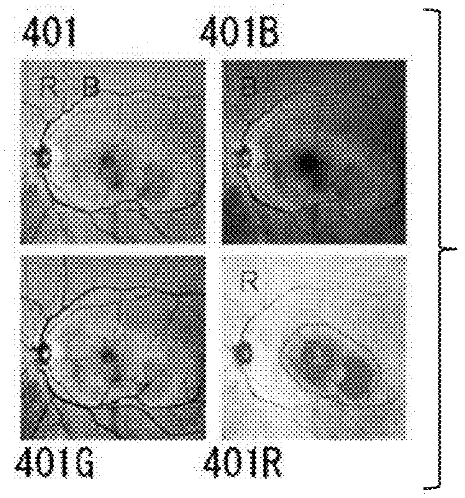
FIGS. 8A to 8C are diagrams showing a case where a monochromatic fundus image is simultaneously displayed as an example of a display mode of a second image, and show the monochromatic fundus image displayed in combination with the second image.
Figure 8B:
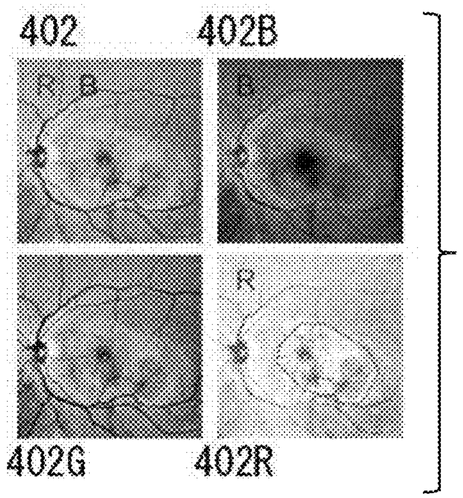

FIGS. 8A and 8B show color fundus images (before correction: 401, after correction: 402) and color component images (before correction: 401R, 401G, and 401B, after correction: 402R, 402G, and 402B) corresponding to respective color components of the color fundus images before and after color gamut correction is performed. In the color component image 402R corresponding to the R component of the second image shown in FIG. 8B, a grayscale value of the R component is corrected through a hue correction process, and as a result, an image that does not originally exist has been drawn in a location (particularly an optic nerve head or a lesion) subjected to correction of a grayscale value surrounded by the dotted line.

Figure 8C:
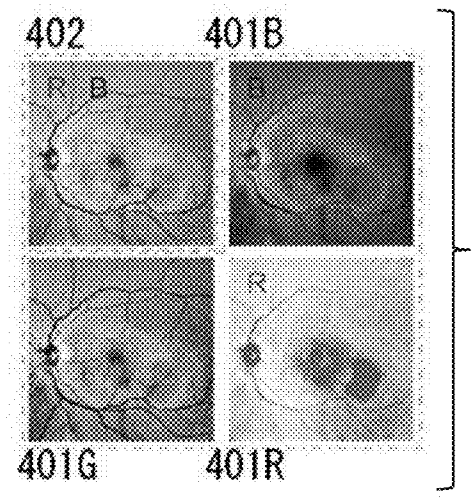

Therefore, in the present example, in a case where the second image is displayed, a combination in FIG. 8C, that is, the second image 402 and the color component images 401R, 401G, and 401B corresponding to respective color components in the first image are simultaneously displayed. As a result, in the present example, an appropriate color component image for at least the R component is displayed. As a result, even in a case where the second image is displayed, an examiner can ascertain a structure of the fundus by using an appropriate color component image.

Modification Example

In the above embodiment, as one of methods of correcting a color gamut (compressing the color gamut), a method of correcting a pixel having color information outside the target color gamut to a color of the color gamut boundary in the target color gamut has been described. However, a method for correcting a color gamut is not necessarily limited to this. For example, the second image may be generated by non-linearly compressing a color gamut as follows.

Figure 9:
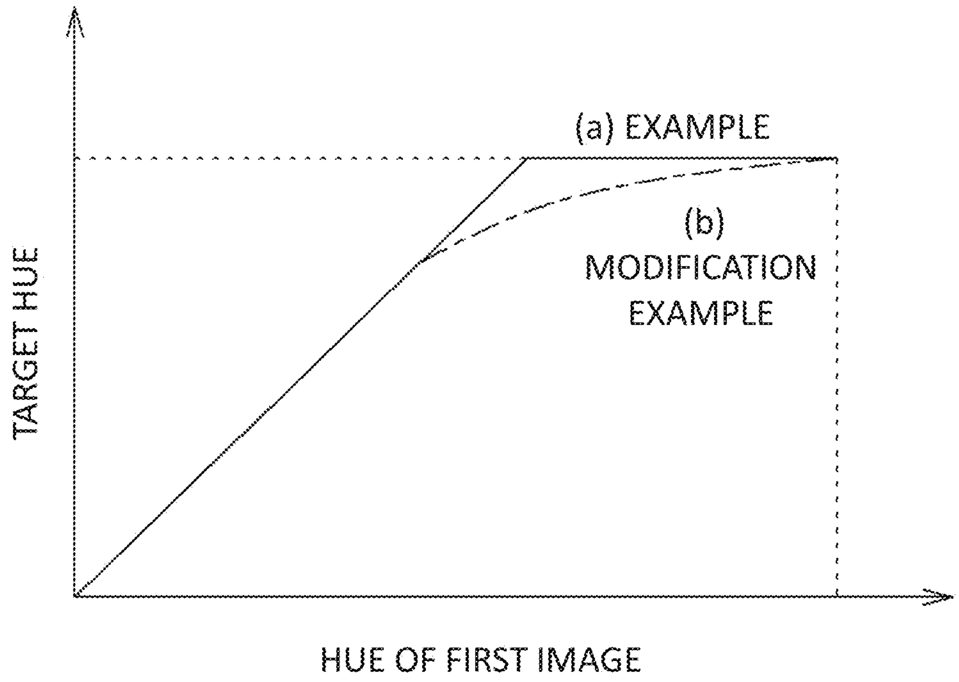
FIG. 9 is a diagram for describing an outline of color gamut correction in a modification example.

A method of non-linearly compressing the color gamut will be described with reference to FIG. 9. In FIG. 9, a hue of the first image in a certain hue (for example, the hue H) is shown on the horizontal axis, and a target hue (a target value of a hue) specified by color gamut information is shown on the vertical axis.

In the method of the above-described Example, a color in the target color gamut is used without replacement, and a color outside the target color gamut is replaced with a color of the target color gamut boundary. In contrast, the method of the present modification example is a method in which a difference in hue outside the target color gamut is reflected in a corrected image by replacing a color in the target color gamut with another color. In this case, the following equation (5) may be applied to the hue f(H) in the above equation (3).

$$f(H)=\begin{cases} H \quad (H \le H'_G,\ H \ge H'_B) \\ H'_G + 2(H_G - H'_G)\left(\dfrac{1}{1+\exp\left(-\dfrac{H-H'_G}{0.5(H_G-H'_G)}\right)} - 0.5\right) \quad (H'_G < H < 180) \\ H'_B + 2(H_B - H'_B)\left(\dfrac{1}{1+\exp\left(-\dfrac{H-H'_B}{0.5(H_B-H'_B)}\right)} - 0.5\right) \quad (180 \le H < H'_B) \end{cases} \tag{5}$$

Here, a case where a boundary of the color gamut is set as a combination of a straight line with a slope of 1 and a sigmoid curve is described, but this combination is only an example. $H'_G$ indicates a switching point between a straight line and a curve on the green side, and $H'_B$ indicates a switching point between a straight line and a curve on the blue side.

In the above Example, the conversion from the original image to the first image is performed on the basis of a predetermined histogram target pattern for each color component, but is not necessarily limited to this, and at least one of brightness, contrast, gamma, and the like of each color component may be manually adjustable. These parameters may be preset for each device.

Similarly, a value defined by an examiner in advance may also be used for the target color gamut in the conversion from the first image to the second image.

In the above Example, the color gamut of the entire image of the first image is corrected, but the present disclosure is not limited to this, and a color gamut of a partial region of the first image may be corrected. As a partial region, a color gamut of at least an optic nerve head region may be corrected. For example, a color gamut of the optic nerve head region in the first image may be corrected according to the method in the present example, and a color of the first image may be maintained outside the optic nerve head region. A difference in a color tint of the optic nerve head is conspicuous when comparing the first image and the fundus photograph, the color gamut of the optic nerve head region is corrected according to the method in the present embodiment and is expressed in a color of the fundus photograph. Therefore, a sense of discomfort received by an examiner is suppressed. By maintaining the color of the first image outside the optic nerve head region, a lesion portion or the like can be expressed and conspicuous with a color tint different from that of the fundus photograph. In this case, the optic nerve head region may be detected through image processing, may be set manually, or may be set at a predetermined position on an image.

In the above Example, in order to perform color correction using equation (2), the hue H is obtained from R, G, and B according to the conversion formula of equation (1). However, the same result as equation (2) can be obtained without calculating a hue. In this case, a corrected R component R' can be obtained by the following equation (6).

$$R' = \max\left(R,\ \frac{60G + (H_G - 60)B}{H_G},\ \frac{-60B + (H_B - 300)G}{H_B - 360}\right) \tag{6}$$

What is claimed is:

1. A non-transitory computer-readable storage medium storing an ophthalmic image processing program comprising instructions which, when the ophthalmic image processing program is executed by a processor of a computer, cause the computer to perform:

an image acquisition step of acquiring an image as a color fundus image; and a color gamut-corrected image generation step of correcting a pixel value of at least any color component in the image, based on color gamut information for specifying a predetermined color gamut to be applied to a color fundus image, to generate a color gamut-corrected image.

2. The storage medium according to claim 1, wherein the image is a color fundus image captured according to a first imaging method, the color gamut information indicates a color gamut corresponding to a color fundus image captured according to a second imaging method, the first imaging method is an imaging method using a plurality of pieces of monochromatic light having different wavelengths, and the second imaging method is an imaging method using white light.

3. The storage medium according to claim 2, wherein the first imaging method is a confocal method that suppresses scattered light, and the second imaging method is a non-confocal method that is based on a color fundus image acquired by white light.

4. The storage medium according to claim 3, wherein the ophthalmic image processing program comprises instructions which cause the computer to further perform:

an original image acquisition step of acquiring an original image as a color fundus image captured according to the first imaging method; and a color tone-corrected image generation step of converting a pixel value of each color component in the original image according to a process different from the color gamut-corrected image generation step, to generate the image.

5. The storage medium according to claim 4, wherein in the color gamut-corrected image generation step, a pixel value of at least a red component in the image is corrected based on the color gamut information.

6. The storage medium according to claim 3, wherein in the color gamut-corrected image generation step, a pixel value of at least a red component in the image is corrected based on the color gamut information.

7. The storage medium according to claim 1, wherein the color gamut information is defined as a hue section.

8. The storage medium according to claim 1, wherein the color gamut information is set based on a hue of each pixel in the first-image.

9. The storage medium according to claim 1, wherein the ophthalmic image processing program comprises instructions which cause the computer to further perform:

a GUI display step of displaying a GUI for accepting an operation of changing a color gamut specified by the color gamut information; and a color gamut information change step of changing the color gamut information based on a change operation via the GUI.

10. The storage medium according to claim 1, wherein the ophthalmic image processing program comprises instructions which cause the computer to further perform:

an image output step of outputting the color gamut-corrected image and a color component image corresponding to the image to an image output device such that the color component image that is a fundus image for each color component in the image is displayed together with the color gamut-corrected image.

11. An ophthalmic image processing apparatus comprising a processor configured to:

acquire an image as a color fundus image; and correct a pixel value of at least any color component in the image, based on color gamut information for specifying a predetermined color gamut to be applied to a color fundus image, to generate a color gamut-corrected image.

* * * * *